United States Patent [19]

Atherton et al.

[11] 4,128,542
[45] Dec. 5, 1978

[54] PEPTIDE DERIVATIVES

[75] Inventors: Frank R. Atherton, Welwyn Garden City; Michael J. Hall, Welwyn; Cedric H. Hassall, Welwyn; Robert W. Lambert, Welwyn; Peter S. Ringrose, Harston, all of England

[73] Assignee: Hoffmann-La Roche Inc., Nutley, N.J.

[21] Appl. No.: 813,066

[22] Filed: Jul. 5, 1977

[30] Foreign Application Priority Data

Jul. 13, 1976 [GB] United Kingdom ............. 29102/76

[51] Int. Cl.² ...................... C07C 103/52; C07G 7/00
[52] U.S. Cl. ............................ 260/112.5 R; 424/177
[58] Field of Search .............. 260/112.5 R, 112.5 LH; 424/177

[56] References Cited

U.S. PATENT DOCUMENTS 3,826,794  7/1974  Flouret ..................... 260/112.5 LH
3,922,262  11/1975 Umezawa et al. ............ 260/112.5 R
4,016,148  4/1977  Atherton et al. ............. 260/112.5 R Primary Examiner—Delbert R. Phillips
Assistant Examiner—Blondel Hazel
Attorney, Agent, or Firm—Jon S. Saxe; George M. Gould; Frank P. Hoffman

[57] ABSTRACT

There is provided peptide derivatives of the general formula

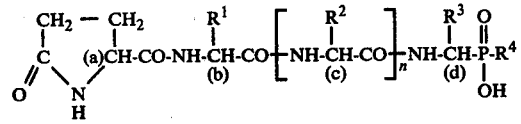

wherein $R^1$, $R^2$ and $R^3$ each represent the characterizing group of an α-amino acid of the type normally found in proteins; $R^4$ represents a hydroxy or methyl group; n stands for zero, 1, 2 or 3; the configuration at the carbon atoms designated as (a), (b) and (c) is L (when $R^1$ or $R^2 \neq$ H); and the configuration at the carbon atom designated as (d) is (R) (when $R^3 \neq$ H)

and pharmaceutically acceptable salts thereof.

The above compounds exhibit antibacterial activity against various microorganisms.

4 Claims, No Drawings

PEPTIDE DERIVATIVES

DESCRIPTION OF THE INVENTION

The present invention relates to peptide derivatives, to a process for the manufacture thereof and to pharmaceutical preparations containing same.

The peptide derivatives provided by the present invention are compounds of the general formula

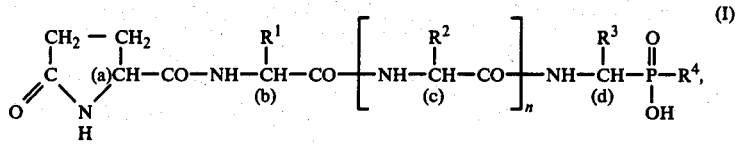

(I)

wherein $R^1$, $R^2$ and $R^3$ each represent the characterising group of an α-amino acid of the type normally found in proteins; $R^4$ represents a hydroxy or methyl group; n stands for zero, 1, 2 or 3; the configuration at the carbon atoms designated as (a), (b) and (c) is L (when $R^1$ or $R^2 \neq H$); and the configuration at the carbon atom designated as (d) is (R) (when $R^3 \neq H$), and pharmaceutically acceptable salts thereof.

As used in this specification, the expression "the characterising group of an α-amino acid of the type normally found in proteins" is used to mean the residue R in an α-amino acid of the general formula

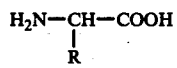

which is of the type normally occurring in proteins and which can be a neutral, an acidic or a basic α-amino acid. Thus, for example, if the amino acid is glycine the residue R represents a hydrogen atom and if the amino acid is alanine the residue R represents the methyl group. In leucine the residue R represents the isobutyl group, in phenylalanine the residue R represents the benzyl group and in glutamic acid the residue R represents the 2-carboxyethyl group. R can also represent a residue which is linked with the amino nitrogen (with the loss of one of the hydrogen atoms attached thereto), thus forming a nitrogen-containing ring such as in proline.

It will be appreciated that when n in formula I stands for 2 or 3, the value of $R^2$ can be the same or different.

When $R^3$ in formula I represents other than a hydrogen atom, the configuration at the carbon atom designated as (d) is (R); that is to say, the configuration which would be obtained by replacing the carboxyl group of an L-amino acid by a phosphorus moiety.

Preferred compounds of formula I are those in which $R^4$ represents a hydroxy group. Also preferred are those compounds of formula I in which n stands for zero or 1. Yet again, compounds of formula I in which $R^1$, $R^2$ and $R^3$ each represent a methyl group are preferred.

Examples of compounds of formula I hereinbefore are:

(1R)-1-(L-pyroglutamyl-L-alanylamino)-ethylphosphonic acid, (1R)-1-(L-pyroglutamyl-L-alanyl-L-alanylamino)-ethylphosphonic acid, (1R)-1-(L-pyroglutamyl-L-methionylamino)-ethylphosphonic acid, and (1R)-1-(L-pyroglutamyl-L-arginylamino)-ethylphosphonic acid.

According to the process provided by the present invention, the peptide derivatives aforesaid (i.e. the compounds of formula I and pharmaceutically acceptable salts thereof) are manufactured by condensing a compound of the general formula

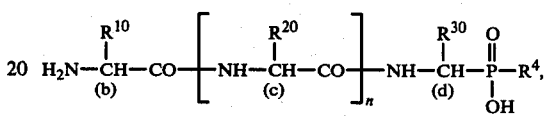

(II)

wherein $R^{10}$, $R^{20}$ and $R^{30}$ have any of the values accorded to $R^1$, $R^2$ and $R^3$ hereinbefore respectively except that any amino group(s) present is (are) protected by a hydrogenolytically-cleavable protecting group, $R^4$ and n have the significance given earlier and the configuration at the carbon atoms designated as (b), (c) and (d) is as specified earlier, with a compound of the general formula

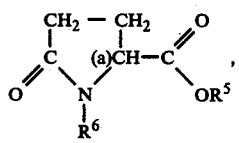

(III)

wherein $R^5$ represents a 2,4,5-trichlorophenyl, pentachlorophenyl or succinimido group, $R^6$ represents a hydrogen atom or an aralkoxycarbonyl group and the configuration at the carbon atom designated as (a) is L, subjecting a condensation product obtained which contains a protected-amino group and/or an aralkoxycarbonyl group $R^6$ to hydrogenolysis and, if desired, converting a compound of formula I obtained into a pharmaceutically acceptable salt.

Examples of hydrogenolytically-cleavable protecting groups which can be used to protect an amino group present in $R^{10}$, $R^{20}$ and/or $R^{30}$ in formula II are aralkoxycarbonyl groups (e.g. benzyloxycarbonyl). An amino group can also be protected by a nitro group as in the case of the nitroarginyl group.

The condensation of a compound of formula II with a compound of formula III can be carried out under conditions which are well-known in peptide chemistry for carrying out condensations, involving activated esters. Thus, for example, the condensation can be carried out in an organic solvent such as aqueous dimethylformamide at a temperature of about 0° C. In a preferred embodiment of the process, a compound of formula II is condensed with a compound of formula III in which $R^5$ represents the 2,4,5-trichlorophenyl group.

A condensation product obtained which contains a protected amino group and/or an aralkoxycarbonyl group $R^6$ is subjected to hydrogenolysis in order to convert the protected amino group into the amino group and to remove the aralkoxycarbonyl group denoted by $R^6$ as the case may be. This hydrogenolysis can be carried out according to methods known per se; for example, in the presence of a noble-metal catalyst such as palladium/carbon or platinum oxide.

The compounds of formula I hereinbefore in which $R^1$, $R^2$ and $R^3$ each represent the characterising group of a neutral or acidic α-amino acid of the type normally found in proteins form salts with pharmaceutically acceptable bases. Examples of such bases are alkali metal hydroxides such as sodium hydroxide. The compounds of formula I in which at least one of $R^1$, $R^2$ and $R^3$ represents the characterising group of a basic α-amino acid of the type normally found in proteins form salts with pharmaceutically acceptable bases (e.g. the aforementioned) and pharmaceutically acceptable strong acids (e.g. hydrochloric acid, hydrobromic acid, sulphuric acid etc). The salts of the compounds of formula I can be obtained by treating a compound of formula I with an appropriate pharmaceutically acceptable base or pharmaceutically acceptable strong acid.

The starting materials of formula II hereinbefore can be prepared, for example, by (a) cleaving off by hydrolysis in accordance with methods known per se the protecting group(s) present in a compound of the general formula

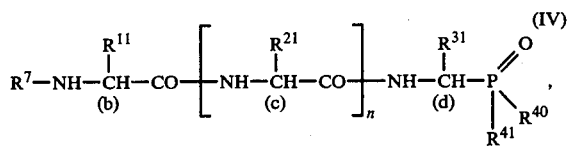

wherein n has the significance given earlier; $R^{11}$, $R^{21}$ and $R^{31}$ have any of the values accorded to $R^1$, $R^2$ and $R^3$ hereinbefore respectively except that any amino group(s) present is (are) protected by a hydrogenolytically cleavable protecting group and any other functional group which may be present is protected by a hydrolytically cleavable protecting group where required; $R^{40}$ represents a methyl group or $R^{41}$; $R^{41}$ represents a hydroxy group or lower alkoxy protecting group; $R^7$ represents a hydrogen atom or a hydrolytically cleavable protecting group; the configuration at the carbon atoms designated as (b) and (c) is L (when $R^{10}$ or $R^{20} \neq$ H) and the configuration at the carbon atom designated as (d) is (R) (when $R^{30} \neq$ H)

(b) separating an (R,S)-diastereomeric compound corresponding to formula II into its diastereomers and isolating the (R)-diastereomer.

Any carboxy or hydroxy group which may be present in $R^{11}$, $R^{21}$ and $R^{31}$ in formula IV can be protected by a conventional hydrolytically cleavable carboxy-protecting or hydroxy-protecting group respectively. For example, a carboxy group may be protected by conversion into an alkyl ester (e.g. a tert.-butyl ester) or an aralkyl ester (e.g. a benzyl ester). Again, for example, a hydroxy group may be protected, for example, by means of an aralkoxycarbonyl group (e.g. benzyloxycarbonyl), an alkanoyl group (e.g. acetyl, propionyl etc), an aroyl group (e.g. benzoyl), an alkyl group (e.g. tert.-butyl) or an aralkyl group (e.g. benzyl. The protection of other functional groups present in $R^{11}$, $R^{21}$ and $R^{31}$ may be carried out in a known manner. Suitably, the protecting group denoted by $R^7$ in formula IV is the tert.-butoxycarbonyl group.

The hydrolytic cleavage of the protecting group or protecting groups present in a compound of formula IV is carried out in accordance with methods known per se; that is to say, methods in actual use for or described in the literature on the hydrolytic cleavage of protecting groups. Thus, for example, the tert.-butoxycarbonyl group may be cleaved off by treatment with a mixture of hydrogen bromide in glacial acetic acid. The tert.-butoxycarbonyl group may also be cleaved off by means of hydrogen chloride in dioxan. A lower alkoxy group denoted by $R^{40}$ and/or $R^{41}$ may be a straight-chain or branched-chain alkoxy group preferably containing from 1 to 6 carbon atoms (e.g. methoxy, ethoxy, propoxy, isopropoxy etc) and may be converted into a hydroxy group by treatment with a mixture of hydrogen bromide in glacial acetic acid or by means of trimethylchlorosilane followed by aqueous hydrolysis. It will be appreciated that the hydrolytic cleavage of the protecting groups can be carried out in a single step or in more than one step depending on the nature of the protecting groups present.

The separation of an (R,S) diastereomeric compound corresponding to formula II into its diastereomers and isolation of the (R)-diastereomer can be carried out according to known methods; for example, by fractional crystallisation or by high pressure liquid chromatography.

The compounds of formula IV hereinbefore may be prepared, for example, by condensing a compound of the general formula

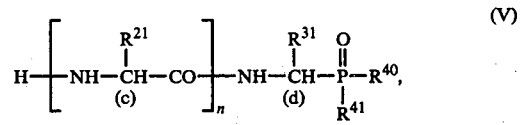

wherein $R^{21}$, $R^{31}$, $R^{40}$, $R^{41}$ and n have the significance given earlier; the configuration at the carbon atom designated as (c) is L (when $R^{21} \neq$ H) and the configuration at the carbon atom designated as (d) is (R) (when $R^{31} \neq$ H), with an appropriately protected α-amino acid, an appropriately protected dipeptide, an appropriately protected tripeptide, an appropriately protected tetrapeptide or a reactive derivative thereof as the case may require.

Thus, when a compound of formula V in which n stands for zero is used, such a compound can be condensed with an appropriately protected α-amino acid or a reactive derivative thereof to give a compound of formula IV in which n stands for zero, or with an appropriately protected dipeptide or a reactive derivative thereof to give a compound of formula IV in which n stands for 1, or with an appropriately protected tripeptide or a reactive derivative thereof to give a compound of formula IV in which n stands for 2 or with an appropriately protected tetrapeptide or a reactive derivative thereof to give a compound of formula IV in which n stands for 3.

Again, a compound of formula V in which n stands for 1 can be condensed with an appropriately protected α-amino acid or a reactive derivative thereof to give a compound of formula IV in which n stands for 1, or with an appropriately protected dipeptide or a reactive derivative thereof to give a compound of formula IV in which n stands for 2 or with an appropriately protected tripeptide or a reactive derivative thereof to give a compound of formula IV in which n stands for 3.

Yet again, a compound of formula V in which n stands for 2 can be condensed with an appropriately protected α-amino acid or a reactive derivative thereof to give a compound of formula IV in which n stands for 2 or with an appropriately protected dipeptide or a reactive derivative thereof to give a compound of formula IV in which n stands for 3.

Finally, a compound of formula V in which n stands for 3 can be condensed with an appropriately protected α-amino acid or a reactive derivative thereof to give a compound of formula IV in which n stands for 3.

Alternatively, the compounds of formula IV can be prepared by carrying out the foregoing condensation using an (R,S) compound corresponding to formula V and separating the (R) compound from the resulting (R,S) product in a manner known per se; for example, by crystallisation, chromatography or fractional crystallisation using a suitable base such as benzylamine.

The aforementioned condensation can be carried out in accordance with methods which are known per se in peptide chemistry; for example, by the mixed anhydride, azide, activated ester or acid chloride method.

In one method, an appropriate compound of formula V can be condensed with an appropriately protected α-amino acid, di-, tri- or tetrapeptide as the case may require in which the terminal carboxy function is a mixed anhydride residue formed with an organic or inorganic acid. Suitably, such an α-amino acid, di-, tri- or tetrapeptide carrying a free carboxy function is treated with a tertiary base such as a tri-(lower alkyl) amine (e.g. triethylamine) or N-ethylmorpholine in an inert organic solvent (e.g. tetrahydrofuran, 1,2-dimethoxyethane, dichloromethane, toluene, petroleum ether or mixtures thereof) and the resulting salt is reacted with a chloroformic acid ester (e.g. the ethyl or isobutyl ester) at a low temperature. The mixed anhydride obtained is then suitably condensed in situ with the compound of formula V.

In another method, an appropriate compound of formula V can be condensed with an appropriately protected α-amino acid, di-, tri- or tetrapeptide as the case may require in which the terminal carboxy group is in the form of an acid azide. This condensation is preferably carried out in an inert organic solvent such as dimethylformamide or ethyl acetate at a low temperature.

In yet another method, an appropriate compound of formula V can be condensed with an appropriately protected α-amino acid, di-, tri- or tetrapeptide as the case may require in which the terminal carboxy function is in the form of an active ester group (e.g. the p-nitrophenyl, 2,4,5-trichlorophenyl or succinimido ester group). This condensation is suitably carried out either in an inert organic solvent such as dimethylformamide or, in the case where $R^{40}$ and/or $R^{41}$ represents a lower alkoxy group, in an aqueous alkanol (e.g. aqueous ethanol).

In a further method, an appropriate compound of formula V can be condensed with an appropriately protected α-amino acid, di-, tri- or tetrapeptide as the case may require in which the terminal carboxy function is in the form of an acid chloride. This condensation is preferably carried out in the presence of a base and at a low temperature.

The starting materials of formula III hereinbefore can be prepared, for example, by reacting L-pyroglutamic acid or an N-aralkoxycarbonyl-L-pyroglutamic acid with 2,4,5-trichlorophenol, pentachlorophenol or N-hydroxysuccinimide in the presence of N,N'-dicyclohexylcarbodiimide and in the presence of an inert organic solvent such as dimethylformamide. Where a N-aralkoxycarbonyl-L-pyroglutamic acid is used in this reaction, the resulting compound of formula III in which $R^6$ represents an aralkoxycarbonyl group can be hydrogenolysed in the manner described earlier to give a corresponding compound of formula III in which $R^6$ represents a hydrogen atom. Where a compound of formula III in which $R^5$ represents a succinimido group and $R^6$ represents a hydrogen atom is used, such a compound is preferably formed in situ in the condensation mixture.

The peptide derivatives provided by this invention possess an antibacterial activity against organisms such as Streptococcus faecalis and Haemophilus influenzae. Thus, for example, (1R)-1-(L-pyroglutamyl-L-alanylamino)-ethylphosphonic acid has a minimum inhibitory concentration (M.I.C.) in μg/ml of 1.0 in an in vitro test against Streptococcus faecalis O-G FS5. Again, for example, (1R)-1-(L-pyroglutamyl-L-alanyl-L-alanylamino)-ethylphosphonic acid has a minimum inhibitory concentration (M.I.C.) in μg/ml of 0.5 in an in vitro test against Streptococcus faecalis O-G FS5 and of 4.0 in an in vitro test against Haemophilus influenzae NCTC 4560.

The peptide derivatives of this invention may accordingly be used as medicaments; for example, in the form of pharmaceutical preparations which contain them in association with a compatible pharmaceutical carrier material. This carrier material can be an inorganic or organic inert carrier material suitable for enteral (e.g. oral) or parenteral administration such as, for example, water, lactose, starch, magnesium stearate, gum arabic, gelatin, polyalkyleneglycols, petroleum jelly etc. The pharmaceutical preparations can be made up in a solid form (e.g. as tablets, dragées, suppositories or capsules) or in a liquid form (e.g. as solutions, suspensions or emulsions). The pharmaceutical preparations which can be prepared according to methods known per se may be sterilised and may contain adjuvants such as preservatives, stabilisers, wetting agents or salts for altering the osmotic pressure.

As is indicated above, compounds of formula I and the salts thereof have the property of adversely affecting the growth of certain microorganisms. They, therefore, would be useful in wash solutions of sanitary purposes as in the washing of hands and the cleaning of equipment, floors or furnishings of contaminated rooms of laboratories. They would also be useful for suppressing the growth of sensitive organisms in plate assays and other microbiological media.

The following Examples illustrate the process provided by the present invention:

EXAMPLE 1

1.96 g (10 mmol) of (1R)-1-(L-alanylamino)-ethylphosphonic acid were stirred in 10 ml of water and treated with 2.8 ml (20 mmol) of triethylamine. 20 ml of dimethylformamide were then added, the solution was cooled to 0° C and stirred while 3.70 g (12 mmol) of the 2,4,5-trichlorophenyl ester of L-pyroglutamic acid were added in the form of a solid. The resulting mixture was stirred for 3 hours at 0° C and then overnight at room temperature. The thus-obtained almost clear solution was evaporated under reduced pressure to give a gum which was partitioned between 50 ml of chloroform and 50 ml of water. The aqueous layer was extracted with a further 30 ml of chloroform. The chloroform extracts were back-washed with 30 ml of water. The aqueous extracts were further extracted with 50 ml of ether and then with 30 ml of ether. The combined aqueous extracts were passed down a column of a sulfonated polystyrene cation exchange resin (Zerolit 225; freshly regenerated in the acid cycle) and the column was eluted with water. The acid eluate (ca. 300 ml) was titrated to pH 4.5 with 4 N aqueous benzylamine. The solution was evaporated and re-evaporated with ethanol and then with ether. The residue was triturated with ether to give 3.43 g of a solid of melting point 210°–214° C (decomposition). Recrystallisation from a mixture of 6 ml of water and 30 ml of acetone gave 1.73 g of the hygroscopic monobenzylamine salt of (1R)-1-(L-pyroglutamyl-L-alanylamino)-ethylphosphonic acid of melting point 223°–226° C; $[\alpha]_D^{20} = -52.3°$ (c = 1% in water).

EXAMPLE 2

In a manner analogous to that described in the first paragraph of Example 1, from 2.67 g (10 mmol) of (1R)-1-(L-alanyl-L-alanylamino)-ethylphosphonic acid, 2.8 ml (20 mmol) of triethylamine and 3.70 g (12 mmol) of the 2,4,5-trichlorophenyl ester of L-pyroglutamic acid there were obtained ca. 2.7 g of a solid benzylamine salt of melting point 244°–250° C. After recrystallisation from a mixture of 5 ml of water, 25 ml of ethanol and 150 ml of ether, there were obtained 2.11 g of a slightly hygroscopic solid of melting point 255°–257° C (decomposition); $[\alpha]_D^{20} = -80.9°$ (c = 0.5% in water). Recrystallisation of a 0.5 g sample of the latter solid from a mixture of 1.5 ml of water, 10 ml of ethanol and 15 ml of ether gave 0.36 g of the monobenzylamine salt of (1R)-1-(L-pyroglutamyl-L-alanyl-L-alanylamino)-ethylphosphonic acid in the form of a gelatinous solid of melting point 259°–263° C decomposition).

EXAMPLE 3

2.56 g (10 mmol) of (1R)-1-(L-methionylamino)-ethylphosphonic acid were stirred in 20 ml of water and treated with 2.8 ml (20 mmol) of triethylamine followed by 20 ml of dimethylformamide. The mixture was cooled to 0° C and 4.63 g (15 mmol) of the 2,4,5-trichlorophenyl ester of L-pyroglutamic acid were added in the form of a solid, which was washed in with 20 ml of cold (0° C) dimethylformamide. The mixture was stirred at 0° C, allowed to warm to room temperature and then stirred at room temperature for a further 24 hours. The mixture was then filtered in order to remove a small amount of solid (0.27 g) and the filtrate was evaporated to dryness. The residue was partitioned between 75 ml of water and 50 ml of chloroform and the aqueous layer was extracted with 50 ml of chloroform. The combined chloroform solutions were back-washed with 50 ml of water. The aqueous extracts were then similarly extracted with ether. The combined aqueous extracts were evaporated to low bulk, the residue was taken up in 30 ml of water and the solution passed down a column of a sulfonated polystyrene cation exchange resin (Zerolit 225; freshly regenerated in the acid cycle) and the column was eluted with water. The acid eluate (ca. 500 ml) was concentrated to ca. 100 ml and titrated to pH 4.5 with 1 M aqueous benzylamine. The solution obtained was evaporated to dryness, ethanol and the mixture re-evaporated. There was obtained a white solid which was recrystallised from a mixture of 30 ml of hot water and 150 ml of ethanol, a small amount of insoluble material being initially filtered off. After refrigeration, there was obtained a flocculent white precipitate which was filtered off, washed successively with ethanol and ether and dried in vacuo to give 2.34 g of the monobenzylamine salt of (1R)-1-(L-pyroglutamyl-L-methionylamino)-ethylphosphonic acid of melting point 235°–238° C (decomposition); $[\alpha]_D^{20} = -34.3°$ (c = 0.57% in water).

The (1R)-1-(L-methionylamino)-ethylphosphonic acid used as the starting material can be prepared, for example, as follows: 12.5 g (0.1 mol) of (1R)-1-aminoethylphosphonic acid were stirred in 100 ml of water and 2.8 ml (0.2 mol) of triethylamine were added. The solution was cooled to 5° C, 100 ml of dimethylformamide were added and the mixture was cooled to 0° C. The mixture was stirred at 0° C and 41.5 g (0.12 mol) of the N-hydroxysuccinimide ester of tert.-butoxycarbonyl-L-methionine were added in one portion in the form of a solid, which was washed in with 100 ml of dimethylformamide. The mixture was stirred at 0° C for 3 hours and then at room temperature for 16 hours. The mixture was filtered in order to remove a small amount (0.52 g) of solid which was washed with water and discarded. The filtrate and washings were combined and evaporated under an oil-pump vacuum at a temperature below 35° C to give an oil. This oil was taken up in 200 ml of water, there being obtained a cloudy solution which was filtered. The filtrate was acidified with 150 ml of 2 N hydrochloric acid and the solution extracted with ether, the ether extract being back-washed with water. The aqueous extracts were combined, left to stand at room temperature for 2 days and then evaporated to give an oil which was taken up in 300 ml of methanol and treated with five 10 ml portions of propylene oxide at 15 minute intervals until the pH remained permanently at 5. A white precipitate formed. This was left to stand at room temperature overnight, filtered off and washed with methanol. The crude product thus obtained was stirred with ethanol and then with ether and subsequently dried to give 23.8 g of solid of melting point 228°–232° C (decomposition). Recrystallisation from water/isopropanol gave 15.9 g (62%) of (1R)-1-(L-methionylamino)-ethylphosphonic acid of melting point 245°–247° C (decomposition); $[\alpha]_D^{20} = -7.4°$ (c = 0.5% in water).

EXAMPLE 4

4.55 g (14 mmol) of (1R)-1-(L-nitroarginylamino)-ethyl-phosphonic acid were taken up in a mixture of 25 ml of water and 2.83 g (28 mmol) of triethylamine and the resulting solution was treated with 25 ml of dimethylformamide and then cooled to 0° C. 6.48 g (21 mmol) of the 2,4,5-trichlorophenyl ester of L-pyroglutamic acid were added in the form of a solid. The mixture obtained was stirred at 0° C for 2 hours and then at room temperature overnight. A small amount of solid was filtered off and the filtrate was evaporated under an oil-pump vacuum. The residue was partitioned between 100 ml of water and 75 ml of chloroform. The chloroform extract was back-washed with 50 ml of water. The aqueous solutions were combined, evaporated to ca 50 ml and passed down a column of a sulfonated polystyrene cation exchange resin (Zerolit 225; freshly regenerated in the acid cycle). Elution with water yielded 500 ml of an acid fraction which was concentrated to ca. 100 ml and then titrated to pH 4.5 with 1 N aqueous benzylamine. The resulting solution was evaporated to dryness to give an oil which was re-evaporated with ethanol to give a sticky solid. This sticky solid was recrystallised from a mixture of 30 ml of water, 150 ml of ethanol and 150 ml of ether, a crystalline gelatinous precipitate being obtained after storage at 0° C. 150 ml of ether were added and the mixture was left to stand at 0° C overnight. The precipitate which formed was filtered off and washed with ethanol and then with ether to give 6.43 g of the monobenzylamine salt of (1R)-1-(L-pyroglutamyl-L-nitroarginylamino)-ethylphosphonic acid of melting point 225°–230° C (decomposition); $[\alpha]_D^{20} = -23.4°$ (c = 0.5% in water).

5.20 g (9.6 mmol) of the aforementioned monobenzylamine salt were taken up in 50 ml of water and passed down a column of a sulfonated polystyrene cation exchange resin (Zerolit 225; 150 g; freshly regenerated in the acid cycle), an acid eluate of 250 ml being collected. To this acid eluate were added 25 ml of glacial acetic acid followed by 1.0 g of palladium-on-charcoal catalyst. The resulting mixture was hydrogenated at room temperature and atmospheric pressure until the uptake of hydrogen ceased. The mixture was filtered and the filter washed well with water. The filtrate and washings were combined and evaporated to give a gum-like solid which was evaporated five times with water and then with n-propanol to give a yellowish-white solid which was triturated with 50 ml of methanol and 50 ml of ether. The resulting pale yellow solid was filtered off, washed with ether and dried to give 3.49 g of a solid of melting point 250° C (decomposition). This solid was recrystallised from a mixture of 75 ml of hot water and 225 ml of isopropanol to give initially an oily product with a small amount of gum at the bottom of the flask. This was triturated and then seeded. There was obtained a white crystalline precipitate which was left to stand at room temperature for 1 hour and at 0° C for 2 hours. The solid obtained was filtered off and washed successively with isopropanol and ether to give 2.78 g of (1R)-1-(L-pyroglutamyl-L-arginylamino)-ethylphosphonic acid as an off-white solid of melting point 271° C (decomposition); $[\alpha]_D^{20} = -38.2°$ (c = 0.52% in water). The filtrate was evaporated and the residue recrystallised from a mixture of 20 ml of water and 80 ml of isopropanol to give a further 0.29 g of (1R)-1-(L-pyroglutamyl-L-arginylamino)-ethylphosphonic acid of melting point 272° C; $[\alpha]_D^{20} = -39.1°$ (c = 0.51% in water).

The (1R)-1-(L-nitroarginylamino)-ethylphosphonic acid used as the starting material can be prepared, for example, as follows: 23.3 g (66 mmol) of N-benzyloxycarbonyl-L-nitroarginine were taken up in 150 ml of dry dimethylformamide. The solution obtained was stirred and 7.60 g (66 mmol) of N-hydroxysuccinimide were added. The mixture was cooled to 0° C. 15.0 g (73 mmol) of dicyclohexylcarbodiimide were added, the mixture was stirred at 0° C for 2 hours and then stored at 0° C overnight. The mixture was then allowed to warm to room temperature and the solid which separated was filtered off and washed with dimethylformamide. The combined filtrate and washings were evaporated under an oil-pump vacuum to give N-benzyloxycarbonyl-L-nitroarginine succinimido ester which was used immediately in the following step.

6.88 g (55 mmol) of (1R)-1-aminoethylphosphonic acid in 50 ml of water were stirred and 11.1 g (110 mmol) of triethylamine followed by 50 ml of dimethylformamide were added. The solution was cooled to 0° C and ca. 60 mmol of the ester, prepared as described in the preceding paragraph, in 50 ml of dimethylformamide were rapidly added dropwise. The mixture was stirred at 0° C for 2 hours, then allowed to come to room temperature and subsequently stirred at room temperature overnight. The mixture was filtered and the solid was washed with water/dimethylformamide (1:1). The combined filtrate and washings were evaporated under an oil-pump vacuum at a bath temperature below 30° C to give a viscous oil which was triturated with 100 ml of methanol and then left to stand at room temperature, there being obtained a white precipitate. This precipitate was filtered off and the filtrate was diluted with 50 ml of water. The solution obtained was passed down a column of a sulfonated polystyrene cation exchange resin (Zerolit 225; freshly regenerated in the acid cycle) made up in water/methanol (1:2). Elution with water/methanol (1:2) yielded an acid fraction which was evaporated to dryness. The residue was partitioned between 150 ml of water and 75 ml of ethyl acetate. The ethyl acetate layer was back-washed with 50 ml of water and the aqueous extracts were combined (aqueous extract I). The ethyl acetate layer was washed with two 100 ml portions of water and the aqueous extracts were combined (aqueous extract II). Aqueous extract I was concentrated to ca. 75 ml, treated with 150 ml of methanol and the resulting solution was titrated to pH 4.5 with 4 M aqueous benzylamine. The solution was evaporated to dryness and the residue taken up in 150 ml of methanol. The solution obtained was dried over sodium sulphate and filtered. The filtrate was treated with 200 ml of ether, there being initially obtained a turbid solution and then an oily gum. This was triturated and left to stand at 0° C to give a flocculent crystalline precipitate. The mixture was stored at 0° C overnight, filtered and the filter cake washed with methanol/ether and then with ether to give 6.29 g of the monobenzylamine salt of (1R)-1-(N-benzyloxycarbonyl-L-nitroarginyl)-ethylphosphonic acid of melting point 182°–192° C. Similar treatment of aqueous extract II and crystallisation from a mixture of 75 ml of methanol and 75 ml of ether gave 2.59 g of the monobenzylamine salt of (1R)-1-(N-benzyloxycarbonyl-l-nitroarginyl)-ethylphosphonic acid of melting point 194°–200° C.

8.88 g (15.7 mmol) of the monobenzylamine salt of (1R)-1-(N-benzyloxycarbonyl-L-nitroarginyl)-ethylphosphonic acid were stirred in 45% hydrogen bromide in glacial acetic acid (15 ml) for 6 hours and then left to stand overnight. 100 ml of ether were added and the supernatant was decanted from the resulting gum. The gum was extracted with 100 ml of ether. The gum was then taken up in 100 ml of methanol and three 5 ml portions of propylene oxide were added while stirring until a permanent pH of 5 was attained. The resulting mixture was stirred at room temperature for 1 hour. The solid was filtered off and washed with methanol to give 4.55 g of (1R)-1-(L-nitroarginylamino)-ethylphosphonic acid of melting point 205°–210° C; $[\alpha]_D^{20} = -12.7°$ (c = 0.5% in water).

The following Example illustrates a typical pharmaceutical preparation containing a peptide derivative provided by the present invention:

EXAMPLE A

A 1000 ml injection solution containing the following ingredients was prepared:

| Ingredient | Per 1000 ml |
|---|---|
| Peptide derivative | 100.0 g |
| Chlorocresol | 1.0 g |
| Acetic acid (glacial) | 1.2 g |
| Sodium hydroxide solution (0.1 N) | q.s. ad pH 4.5 |
| Water for injection | ad 1000 ml |

The peptide derivative was dissolved in 500 ml of water for injection. The chlorocresol was dissolved in 200 ml of water for injection and added to the first solution. The acetic acid was then added while stirring. A 0.1 N solution of sodium hydroxide in water for injection was added while stirring until a pH of 4.5 was obtained. The resulting solution was then made up to 1000 ml with water for injection, filtered through a 0.22 micron membrane filter and filled into ampoules which were sealed and sterilised in an autoclave at 121° C. for 20 minutes.

We claim:
1. (1R)-1-(L-Pyroglutamyl-L-alanylamino)-ethylphosphonic acid.
2. (1R)-1-(L-Pyroglutamyl-L-alanyl-L-alanylamino)-ethylphosphonic acid.
3. (1R)-1-(L-Pyroglutamyl-L-methionylamino)-ethylphosphonic acid.
4. (1R)-1-(L-Pyroglutamyl-L-arginylamino)-ethylphosphonic acid.

* * * * *